(12) United States Patent
Auld et al.

(10) Patent No.: US 9,510,848 B2
(45) Date of Patent: *Dec. 6, 2016

(54) TARGETED ILLUMINATION FOR SURGICAL INSTRUMENT

(71) Applicant: Novartis AG, Basel (CH)

(72) Inventors: Jack Robert Auld, Laguna Niguel, CA (US); Ronald T. Smith, Irvine, CA (US)

(73) Assignee: Novartis AG, Basel (CH)

( * ) Notice: Subject to any disclaimer, the term of this patent is extended or adjusted under 35 U.S.C. 154(b) by 219 days.

This patent is subject to a terminal disclaimer.

(21) Appl. No.: 14/495,139

(22) Filed: Sep. 24, 2014

(65) Prior Publication Data

US 2015/0011839 A1  Jan. 8, 2015

Related U.S. Application Data

(63) Continuation of application No. 12/014,151, filed on Jan. 15, 2008, now Pat. No. 9,402,643.

(51) Int. Cl.

| | | |
|---|---|---|
| *A61B 18/18* | (2006.01) | |
| *A61N 5/06* | (2006.01) | |
| *A61B 17/32* | (2006.01) | |
| *A61B 17/28* | (2006.01) | |
| *A61B 17/3201* | (2006.01) | |
| *A61B 17/3207* | (2006.01) | |

(Continued)

(52) U.S. Cl.
CPC ..... *A61B 17/320016* (2013.01); *A61B 1/0669* (2013.01); *A61B 1/07* (2013.01); *A61B 17/28* (2013.01); *A61B 17/3201* (2013.01); *A61B 17/320783* (2013.01); *A61B 90/30* (2016.02); *A61B 2090/306* (2016.02); *A61F 9/007* (2013.01)

(58) Field of Classification Search
CPC .............. A61B 17/28; A61B 17/3201; A61B 17/320783; A61B 17/320016; A61B 17/3421; A61B 1/07; A61B 1/0669; A61B 90/30; A61B 2090/306; A61F 9/007; A61F 9/00736; A61F 9/00763

See application file for complete search history.

(56) References Cited

U.S. PATENT DOCUMENTS

| | | |
|---|---|---|
| 3,089,484 A | 5/1963 | Hett |
| 3,093,134 A | 6/1963 | Roehr |

(Continued)

FOREIGN PATENT DOCUMENTS

| | | |
|---|---|---|
| DE | 19957785 A1 | 6/2000 |
| EP | 0684016 A2 | 11/1995 |

(Continued)

OTHER PUBLICATIONS

International Search Report and Written Opinion of the International Searching Authority, International Application No. PCT/2013/067083, Jan. 16, 2014, 9 pages.

(Continued)

*Primary Examiner* — Gary Jackson
*Assistant Examiner* — Boniface N Nganga
(74) *Attorney, Agent, or Firm* — Darien Reddick

(57) ABSTRACT

An illuminated surgical instrument has a working area located near an end of the instrument. An array of optical fibers terminates near the end of the instrument. The array of optical fibers is located adjacent to the instrument such that the array of optical fibers provides targeted illumination to the working area only on one side of the instrument.

10 Claims, 8 Drawing Sheets

(51) Int. Cl.
*A61B 1/06* (2006.01)
*A61B 1/07* (2006.01)
*A61F 9/007* (2006.01)

(56) References Cited

U.S. PATENT DOCUMENTS

| | | | |
|---|---|---|---|
| 3,131,690 A | 5/1964 | Innis et al. | |
| 3,385,553 A | 5/1968 | Braun | |
| 3,439,157 A | 4/1969 | Myles | |
| 3,910,677 A | 10/1975 | Becker et al. | |
| 3,932,022 A | 1/1976 | Henning et al. | |
| 3,981,709 A | 9/1976 | Kondo et al. | |
| 3,990,453 A | 11/1976 | Douvas et al. | |
| 4,168,707 A | 9/1979 | Douvas et al. | |
| 4,200,106 A | 4/1980 | Douvas et al. | |
| 4,597,030 A | 6/1986 | Brody | |
| 4,607,622 A | 8/1986 | Fritch et al. | |
| 4,641,912 A | 2/1987 | Goldenberg | |
| 4,678,268 A | 7/1987 | Russo et al. | |
| 4,693,244 A | 9/1987 | Daikuzono | |
| 4,693,556 A | 9/1987 | McCaughan, Jr. | |
| 4,733,933 A | 3/1988 | Pikulski | |
| 4,781,703 A | 11/1988 | Walker et al. | |
| 4,842,390 A | 6/1989 | Sottini et al. | |
| 4,872,837 A | 10/1989 | Issalene et al. | |
| 4,994,047 A | 2/1991 | Walker et al. | |
| 4,995,691 A | 2/1991 | Purcell, Jr. | |
| 5,037,174 A | 8/1991 | Thompson | |
| 5,217,456 A | 6/1993 | Narciso, Jr. | |
| 5,263,952 A | 11/1993 | Grace et al. | |
| 5,312,393 A | 5/1994 | Mastel | |
| 5,351,168 A | 9/1994 | Easley | |
| 5,411,016 A | 5/1995 | Kume et al. | |
| 5,425,730 A | 6/1995 | Luloh | |
| 5,478,338 A | 12/1995 | Reynard | |
| 5,620,639 A | 4/1997 | Stevens et al. | |
| 5,630,809 A * | 5/1997 | Connor | A61B 3/0008 606/17 |
| 5,651,783 A | 7/1997 | Reynard | |
| 5,667,472 A | 9/1997 | Finn et al. | |
| 5,716,320 A | 2/1998 | Buttermore | |
| 5,754,717 A | 5/1998 | Esch | |
| 5,860,996 A | 1/1999 | Urban et al. | |
| 6,080,143 A | 6/2000 | Connor | |
| 6,206,823 B1 | 3/2001 | Kolata et al. | |
| 6,387,044 B1 | 5/2002 | Tachibana et al. | |
| 6,454,744 B1 | 9/2002 | Spohn et al. | |
| 6,939,341 B2 | 9/2005 | Vijfvinkel | |
| 7,473,249 B2 | 1/2009 | Scheller et al. | |
| 7,593,778 B2 | 9/2009 | Chandran et al. | |
| 7,766,904 B2 | 8/2010 | Mc Gowan, Sr. et al. | |
| 7,896,838 B2 | 3/2011 | Devega | |
| 7,901,353 B2 | 3/2011 | Vayser et al. | |
| 8,496,862 B2 | 7/2013 | Zelkovich et al. | |
| 8,900,139 B2 | 12/2014 | Yadlowsky et al. | |
| 8,968,347 B2 | 3/2015 | McCollam | |
| 9,066,678 B2 | 6/2015 | Auld et al. | |
| 9,402,643 B2 | 8/2016 | Auld et al. | |
| 2001/0056278 A1 | 12/2001 | Nield et al. | |
| 2002/0123744 A1 | 9/2002 | Reynard | |
| 2004/0215065 A1 | 10/2004 | Setten | |
| 2005/0080384 A1 | 4/2005 | Green, Jr. | |
| 2005/0135776 A1* | 6/2005 | Vijfvinkel | A61B 17/320016 385/147 |
| 2005/0154379 A1* | 7/2005 | McGowan, Sr. | A61F 9/008 606/4 |
| 2005/0245916 A1* | 11/2005 | Connor | A61F 9/008 606/4 |
| 2006/0135973 A1 | 6/2006 | Hawkins et al. | |
| 2007/0179430 A1 | 8/2007 | Smith et al. | |
| 2008/0108981 A1 | 5/2008 | Telfair | |
| 2008/0147018 A1 | 6/2008 | Squilla et al. | |
| 2008/0179792 A1 | 7/2008 | Kurimoto et al. | |
| 2008/0255545 A1 | 10/2008 | Mansfield et al. | |
| 2009/0030406 A1 | 1/2009 | Hickingbotham | |
| 2009/0131931 A1 | 5/2009 | Lee et al. | |
| 2009/0135280 A1 | 5/2009 | Johnston et al. | |
| 2009/0163897 A1 | 6/2009 | Skinner | |
| 2009/0182313 A1 | 7/2009 | Auld | |
| 2010/0026207 A1 | 2/2010 | Facchini et al. | |
| 2010/0145284 A1 | 6/2010 | Togashi | |
| 2010/0228083 A1 | 9/2010 | Mirza et al. | |
| 2010/0228085 A1 | 9/2010 | Mirza et al. | |
| 2011/0130779 A1 | 6/2011 | Mirza et al. | |
| 2011/0282160 A1 | 11/2011 | Bhadri et al. | |
| 2011/0319839 A1 | 12/2011 | Del Vecchio | |
| 2012/0035425 A1 | 2/2012 | Schaller | |
| 2012/0041461 A1 | 2/2012 | McCollam | |
| 2012/0238830 A1 | 9/2012 | Vukeljic et al. | |
| 2012/0296173 A1 | 11/2012 | Stocks et al. | |
| 2013/0282031 A1 | 10/2013 | Woodard, Jr. et al. | |
| 2014/0100426 A1 | 4/2014 | Barbour | |
| 2014/0121469 A1 | 5/2014 | McCollam et al. | |
| 2014/0210116 A1 | 7/2014 | Schaller | |
| 2014/0357957 A1 | 12/2014 | Bhadri et al. | |
| 2014/0379054 A1 | 12/2014 | Cooper et al. | |
| 2015/0011838 A1 | 1/2015 | Auld et al. | |
| 2015/0011839 A1 | 1/2015 | Auld et al. | |
| 2016/0113722 A1 | 4/2016 | Heeren | |

FOREIGN PATENT DOCUMENTS

| | | |
|---|---|---|
| GB | 1207229 A | 9/1970 |
| GB | 1349881 A | 4/1974 |
| JP | H10234665 | 9/1998 |
| JP | 2000245740 | 9/2000 |
| JP | 2001079010 A2 | 3/2001 |
| JP | 2006-325973 | 12/2006 |
| JP | 2009519766 T2 | 5/2009 |
| JP | 2009148550 A2 | 7/2009 |
| PL | 166358 | 5/1995 |
| WO | 0139705 A1 | 6/2001 |
| WO | 0248017 A1 | 6/2002 |
| WO | 2004002337 A1 | 1/2004 |
| WO | 2007081474 A2 | 7/2007 |
| WO | 2008139982 | 11/2008 |
| WO | 2008139982 A1 | 11/2008 |
| WO | 2009091462 | 7/2009 |

OTHER PUBLICATIONS

PCT International Preliminary Report on Patentability and Written Opinion, Application No. PCT/US2013/67083, Publication No. WO/2014/070664, dated May 5, 2015, 8 pages.
Calhoun, The Roto-Extractor in Pediatric Ophthalmology, Tr. Am. Ophth. Soc., vol. LXXIII, pp. 292-305, 1975.
Chalam, et al., Illuminated Curved Vitrectomy Probe for Vitreoretinal Surgery, Ophthalmic Surgery, Lasers and Imaging, Nov./Dec. 2007—vol. 38 Â—Issue 6: 525-526.
Douvas, Microsurgical Roto-Extractor Instrument for Vitrectomy, Mod. Probl. Ophthal., vol. 15, pp. 253-260 (Karger, Basel 1975).
Fisher et al., Inexpensive Illuminated Vitrectomy Cutter, The Journal of Retinal and Vitreous Diseases, Dec. 2003, vol. 23, Issue 6, p. 891.
International Search Report for PCT/US2011/047262, dated Dec. 12, 2011, 2 pages.
Supplementary European Search Report for PCT/US2011/047262, dated Oct. 9, 2013, 8 pages.
Carron, Fiber Optics in Computer Screens to Save Energy, Feb. 22, 2012, 2 pages, retrieved Oct. 29, 2015 from http://phys.org/news/2012-02-fiber-optics-screens-energy.html.
International Search Report for PCT/US2008/086119, Publication No. WO2009/091462, dated Mar. 30, 2009, 2 pages.
PCT International Preliminary Report on Patentability and Written Opinion of the International Searching Authority, International Application No. PCT/US2008/086119, dated Jul. 20, 2010, 7 pages.
PCT International Preliminary Report on Patentability and Written Opinion, PCT/US2011/046942, dated Feb. 12, 2013, 6 pages.
International Search Report for PCT/US2011/046942, dated Nov. 15, 2011, 4 pages.

(56) References Cited

OTHER PUBLICATIONS

International Search Report and Written Opinion of the International Searching Authority, International Application No. PCT/IB2016/051993, Not yet published, Jun. 16, 2016, 11 pages.

European Search Report for Application No. 13851516.8, Publication No. EP2861125, Published Apr. 22, 2015, 6 pages.

International Search Report and Written Opinion, PCT/US2015/054426, Jan. 8, 2016, 15 pages.

* cited by examiner

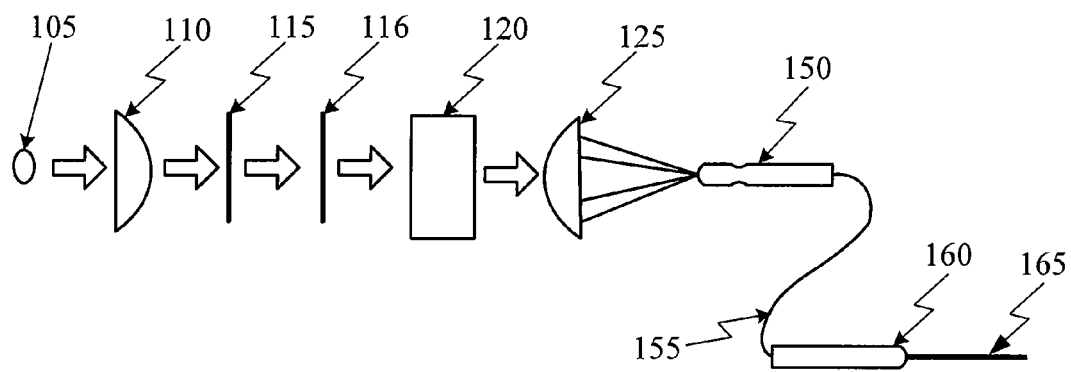
Fig. 1
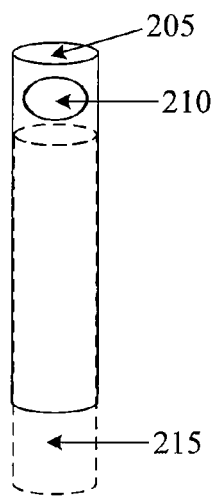 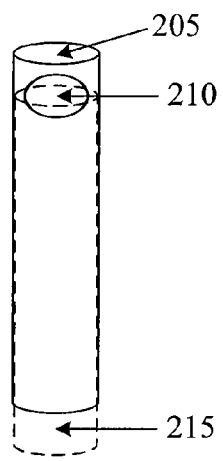
Fig. 2A  Fig. 2B

TARGETED ILLUMINATION FOR SURGICAL INSTRUMENT

CROSS REFERENCE TO RELATED APPLICATIONS

This application is a continuation of prior application Ser. No. 12/014,151, filed Jan. 15, 2008, the entire contents of which are incorporated herein by reference.

BACKGROUND OF THE INVENTION

The present invention relates to an illuminated vitrectomy probe or other illuminated ophthalmic surgical instrument, and more particularly to an optical fiber array configuration designed to provide illumination over a specific area at the working end of an instrument, for example, the cutting port of a vitrectomy probe.

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body (such as a vitrectomy probe—which has a cutting end that is inserted into the eye. A vitrectomy probe has a small gauge needle or cannula with a cutting mechanism on the end that is inserted into the eye).

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is launched at an optical fiber that carries the light into the eye.

To reduce the number of required incisions during vitrectomy surgery and improve the delivery of light to the surgical site, an effort has been made to integrate a light source (typically one or more optical fibers) with a vitrectomy probe. These efforts have been difficult because of the small diameters of vitrectomy probes. It is desirable to make the diameter of the cutting end of the vitrectomy probe as small as possible so that it can be inserted through very small incisions into the eye.

In one case, a ring of optical fibers is disposed around a vitrectomy probe and held in place by a sleeve. This illuminated vitrectomy sleeve consists of a bundle of small diameter optical fibers fed into a hub region and then distributed in a ring pattern. The illuminated vitrectomy sleeve is designed to be a stand-alone device into which the vitrectomy probe is inserted. As such, it must have its own structural strength that is provided by a sandwiching the array of optical fibers between two metal or plastic cylindrical cannulas. Since it is preferable to make the total diameter of the vitrectomy probe and sleeve as small as possible, very little cross-sectional area is left to house the optical fibers. Accordingly, very little light is transmitted into the eye. In addition, the ring of fibers distributes light throughput the entire region adjacent to the distal end of the vitrectomy probe instead of concentrating it on the cutting port opening where it is needed.

In another case, a single fiber may be attached to the vitrectomy needle and held in place with a plastic sleeve. For example, Synergetics, Inc. manufactures a 25 gauge vitrectomy needle with a single optical fiber that is held in place with a plastic sleeve. The plastic sleeve can then fit into a 20 gauge cannula that is inserted into the eye. Very little cross-sectional area is available between the 25 gauge vitrectomy needle and the inner surface of the plastic sleeve (which is typically one or two mils thick). In addition, a larger incision must be made to accommodate the 20 gauge cannula through which the plastic sleeve must fit. Today, it is preferable to keep the incision size small so as to accommodate a probe with a diameter of 23 gauge or smaller. What is needed is an improved illuminated vitrectomy probe that delivers sufficient light into the eye while accommodating these smaller incision sizes.

In addition, the same constraints restrict the feasible size of other ophthalmic surgical instruments. For example, scissors, forceps, aspiration probes, retinal picks, delamination spatulas, various cannulas, and the like may also benefit from targeted illumination. These instruments are designed to fit through small gauge cannulas that are inserted through the sclera during surgery. The same principles used to design an improved illuminated vitrectomy probe can also be used to provide targeted illumination for these other surgical instruments.

SUMMARY OF THE INVENTION

In one embodiment consistent with the principles of the present invention, the present invention is an illuminated vitrectomy probe. The vitrectomy probe has a cutting port disposed at a distal end of a cannula. An array of optical fibers terminates near the cutting port. The array of optical fibers is located adjacent to the cannula only on a side of the cannula on which the cutting port is located.

In another embodiment consistent with the principles of the present invention, the present invention is an illuminated surgical instrument. The instrument has a working area located near an end of the instrument. An array of optical fibers terminates near the end of the instrument. The array of optical fibers is located adjacent to the instrument such that the array of optical fibers provides illumination to the working area only on one side of the instrument.

In another embodiment consistent with the principles of the present invention, the present invention is an illuminated surgical instrument. The instrument has a working area located near an end of the instrument. The working area has an orientation with respect to the end of the instrument. An array of optical fibers terminates near the end of the instrument. The array of optical fibers is located adjacent to the instrument such that the array of optical fibers provides targeted illumination only to the working area. The targeted illumination is configured for the orientation of the working area.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 1 is an unfolded view of an ophthalmic endoilluminator according to an embodiment of the present invention.

FIGS. 2A and 2B are perspective views of a vitrectomy probe according to an embodiment of the present invention.

DETAILED DESCRIPTION OF THE PREFERRED EMBODIMENTS

Figure 3A:
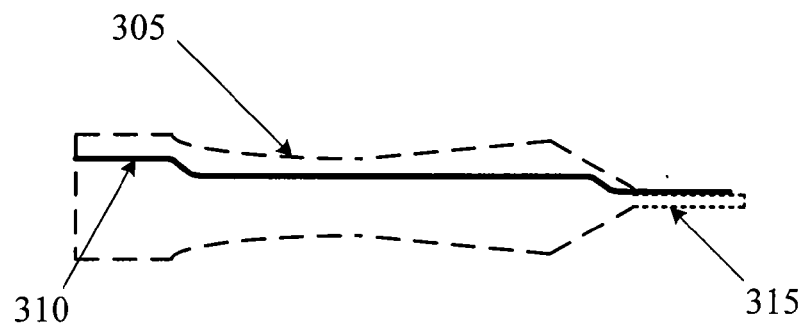
FIG. 3A is a cross section view of a vitrectomy hand piece with an integrated illuminator according to an embodiment of the present invention.

Reference is now made in detail to the exemplary embodiments of the invention, examples of which are illustrated in the accompanying drawings. Wherever possible, the same reference numbers are used throughout the drawings to refer to the same or like parts.

FIG. 1 is an unfolded view of an ophthalmic endoilluminator as used with an illuminated vitrectomy probe according to an embodiment of the present invention. In FIG. 1, the endoilluminator includes light source 105, collimating lens 110, optional cold mirror 115, optional hot mirror 116, attenuator 120, condensing lens 125, connector 150, optical fiber 155, hand piece 160, and vitrectomy probe 165.

The light from light source 105 is collimated by collimating lens 110. The collimated light is reflected and filtered by optional cold mirror 115 and/or transmitted and filtered by optional hot mirror 116. The resulting beam is attenuated by attenuator 120 and focused by condensing lens 125. The focused beam is directed through connector 150 and optical fiber 155 to vitrectomy probe 165 where it illuminates the inside of the eye as described below.

Light source 105 is typically a lamp, such as a mercury vapor lamp, a xenon lamp, a metal halide lamp, or a halogen lamp. Light source 105 is operated at or near full power to produce a relatively stable and constant light output. In one embodiment of the present invention, light source 105 is a xenon lamp with an arc length of about 0.18 mm. Other embodiments of the present invention utilize other light sources such as light emitting diodes (LEDs). One or more LEDs can be operated to produce a constant and stable light output. As is known, there are many types of LEDs with different power ratings and light output that can be selected as light source 105.

Collimating lens 110 is configured to collimate the light produced by light source 105. As is commonly known, collimation of light involves lining up light rays. Collimated light is light whose rays are parallel with a planar wave front.

Optional cold mirror 115 is a dichroic reflector that reflects visible wavelength light and only transmits infrared and ultraviolet light to produce a beam filtered of harmful infrared and ultraviolet rays. Optional hot mirror 116 reflects long wavelength infrared light and short wavelength ultraviolet light while transmitting visible light. The eye's natural lens filters the light that enters the eye. In particular, the natural lens absorbs blue and ultraviolet light which can damage the retina. Providing light of the proper range of visible light wavelengths while filtering out harmful short and long wavelengths can greatly reduce the risk of damage to the retina through aphakic hazard, blue light photochemical retinal damage and infrared heating damage, and similar light toxicity hazards. Typically, a light in the range of about 430 to 700 nanometers is preferable for reducing the risks of these hazards. Optional cold mirror 115 and optional hot mirror 116 are selected to allow light of a suitable wavelength to be emitted into an eye. Other filters and/or dichroic beam splitters may also be employed to produce a light in this suitable wavelength range. For example, holographic mirrors may also be used to filter light.

Attenuator 120 attenuates or decreases the intensity of the light beam. Any number of different attenuators may be used. For example, mechanical louvers, camera variable aperture mechanisms, or neutral density filters may be used. A variable-wedge rotating disk attenuators may also be used.

Condensing lens 125 focuses the attenuated light beam so that it can be launched into a small diameter optical fiber. Condensing lens 125 is a lens of suitable configuration for the system. Condensing lens 125 is typically designed so that the resulting focused beam of light can be suitably launched into and transmitted by an optical fiber. As is commonly known, a condensing lens may be a biconvex or plano-convex spherical or aspheric lens. In a plano-convex aspheric lens, one surface is planar and the other surface is convex with a precise aspheric surface in order to focus the light to a minimum diameter spot.

The endoilluminator that is handled by the ophthalmic surgeon includes connector 150, optical fiber 155, hand piece 160, and illuminated vitrectomy probe 165. Connector 150 is designed to connect the optical fiber 155 to a main console (not shown) containing light source 105. Connector 150 properly aligns optical fiber 155 with the beam of light that is to be transmitted into the eye. Optical fiber 155 is typically a small diameter fiber that may or may not be tapered. Hand piece 160 is held by the surgeon and allows for the manipulation of illuminated vitrectomy probe 165 in the eye.

FIGS. 2A and 2B are perspective views of a vitrectomy probe according to an embodiment of the present invention. In a typical vitrectomy probe, an outer cannula 205 includes port 210. An inner piston 215 reciprocates in cannula 205. One end of piston 215 is configured so that it can cut vitreous when as it enters port 210. As shown in FIGS. 2A and 2B, piston 215 moves up and down in cannula 205 to produce a cutting action. Vitreous enters port 210 when the vitrectomy probe is in the position shown in FIG. 2A. The vitreous is cut as piston 215 moves upward closing off port 210 as shown in FIG. 2B. While most of the details of a vitrectomy probe are omitted, it is important to note that the cutting of the vitreous takes place at port 210. Accordingly, it would be desirable to concentrate illumination around port 210, so that a surgeon can see the vitreous being cut (as well as other eye structures near the cutting mechanism).

FIG. 3A is a cross section view of a vitrectomy hand piece with an integrated illuminator according to an embodiment of the present invention. In FIG. 3A, an array of optical fibers 310 is located in vitrectomy hand piece housing 305. Optical fiber array 310 exits the hand piece housing 305 at a small opening adjacent to cannula 315. Cannula 315 is similar in structure and operation to cannula 205 of FIGS. 2A and 2B.

Figure 3B:
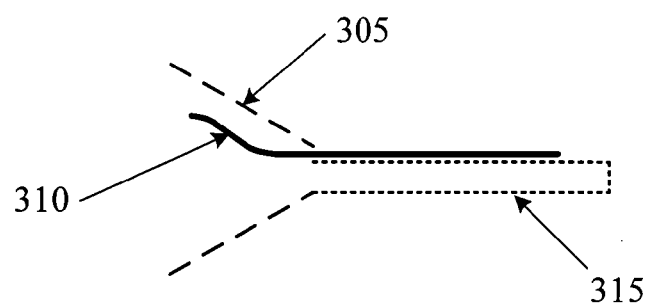
FIG. 3B is an exploded cross section view of a vitrectomy hand piece with an integrated illuminator according to an embodiment of the present invention.

FIG. 3B is an exploded cross section view of a vitrectomy hand piece with an integrated illuminator according to an embodiment of the present invention. FIG. 3B more clearly shows the orientation of optical fiber array 310 with respect to hand piece housing 305 and cannula 315. Optical fiber array 310 exits hand piece housing 305 through a small opening adjacent to cannula 315. Optical fiber array 310 is arranged at a distal end of cannula 315 as depicted in FIGS. 5, 7, 9A, and 9B. The small opening in hand piece housing 305 through which optical fiber array 310 passes may be sealed.

Figure 4:
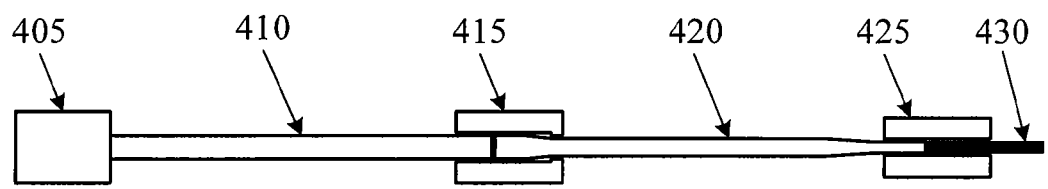
FIG. 4 is a cross section view of an illuminator optical fiber path according to an embodiment of the present invention.

FIG. 4 is cross section view of an illuminator optical fiber path according to an embodiment of the present invention. In the embodiment of FIG. 4, a standard 20 gauge ACMI connector 405 is coupled to a proximally belled. 0.0295 inch, 0.5 NA or 0.63 NA optical fiber 410. Optical fiber 410 is coupled to a belled, stretched 0.63 NA optical fiber 420 via a 25 gauge coupling 415. A second coupling 425 couples optical fiber 420 to an array of optical fibers 430. While a specific example is provided in FIG. 4, numerous other configurations of optical fibers and couplers may be employed to implement the illuminated vitrectomy probe of the present invention.

Figure 5:
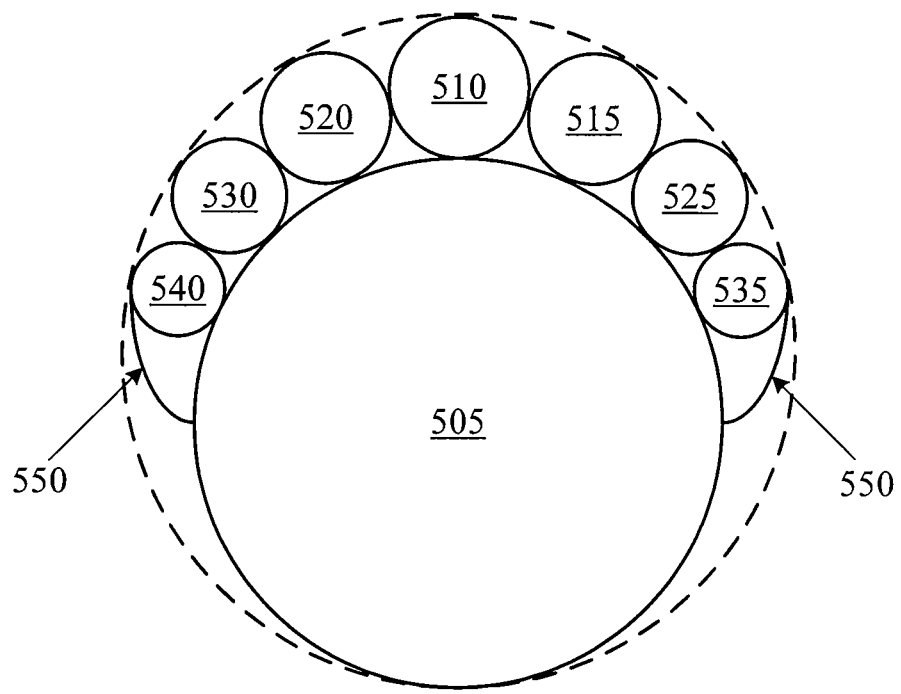
FIG. 5 is a cross section view of a distal end of an illuminated vitrectomy probe according to an embodiment of the present invention.

FIG. 5 is cross section view of a distal end of an illuminated vitrectomy probe according to an embodiment of the present invention. FIG. 5 shows the arrangement of an array of optical fibers at a distal or cutting end of a vitrectomy probe. This arrangement of optical fibers is designed to produce illumination at the cutting port of a vitrectomy probe. The view in FIG. 5 is a cross section view or slice of the vitrectomy probe perpendicular to the axis along which the cannula lies. In this example, seven optical fibers 510, 515, 520, 525, 530, 535, and 540 (or optical fiber array) are arranged around vitrectomy probe 505 as shown. In the embodiment of FIG. 5, optical fiber array 510, 515, 520, 525, 530, 535, and 540 is potted into place against the upper surface of vitrectomy probe needle 505. Vitrectomy probe 505, in this case, is a 25 gauge probe—that is, its cannula is a 25 gauge cannula. The dashed circle represents a 23 gauge cannula through which the vitrectomy probe 505 and optical fiber array (seven optical fibers—510, 515, 520, 525, 530, 535, and 540) pass in order to enter the eye. In this manner, the vitrectomy cutting function and the illumination function—both of which are required for surgery—are provided in a small diameter package that fits through a 23 gauge cannula. This small 23 gauge cannula is desirable because smaller incision sizes in the eye generally result in fewer complications.

In the embodiment of FIG. 5, optical fiber array 510, 515, 520, 525, 530, 535, and 540 is comprised of fibers ranging in size from 0.00345 inches in diameter (535 and 540) to 0.0049 inches in diameter (510). Optical fibers 515 and 520 have a diameter of 0.0047 inches, and optical fibers 525 and 530 have a diameter of 0.00415 inches. In this case, optical fiber array 510, 515, 520, 525, 530, 535, and 540 provides a cross section area available for illumination of about 60,500 square microns. As such, this configuration emits about 16 lumens (using an AHBI illuminator with 100% efficiency at the coupling)—all of which is concentrated around the cutting port of the vitrectomy probe.

Figure 6:
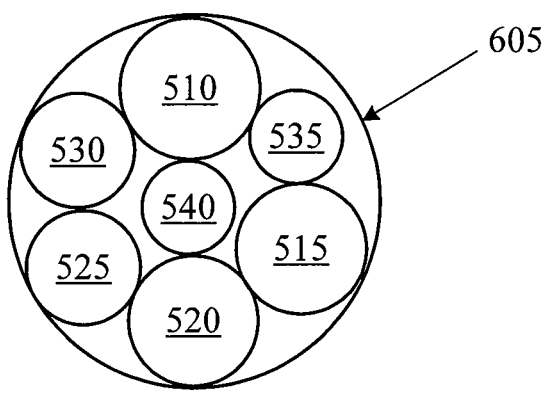
FIG. 6 is a cross section view of an optical fiber array used with an illuminated vitrectomy probe according to an embodiment of the present invention.

FIG. 6 is a cross section view of an optical fiber array used with an illuminated vitrectomy probe according to an embodiment of the present invention. The embodiment of FIG. 6 depicts the proximal end of optical fiber array 510, 515, 520, 525, 530, 535, and 540. This end of optical fiber array 510, 515, 520, 525, 530, 535, and 540 is coupled to the 0.63 NA optical fiber 420 as depicted in FIG. 4. In FIG. 6, 605 represents the diameter of the 0.63 NA optical fiber core. Each of the optical fibers in optical fiber array 510, 515, 520, 525, 530, 535, and 540 typically have a core and cladding. In FIG. 6, the proximal end of the optical fiber cores of optical fiber array 510, 515, 520, 525, 530, 535, and 540 fit within 605 (representing the core of the 0.63 NA optical fiber).

Figure 7:
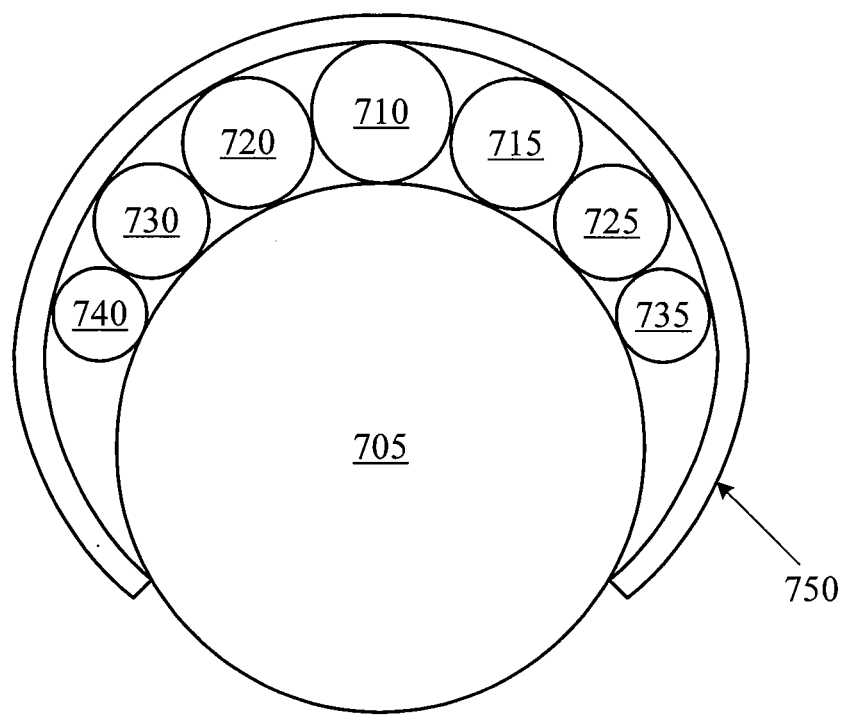
FIG. 7 is a cross section view of a distal end of an illuminated vitrectomy probe according to an embodiment of the present invention.

FIG. 7 is a cross section view of a distal end of an illuminated vitrectomy probe according to an embodiment of the present invention. In the embodiment of FIG. 7, a sleeve 750 (in this case a polyimide sleeve with a 1 mil thickness—though any sleeve may be used) holds optical fiber array 710, 715, 720, 725, 730, 735, and 740 in place against vitrectomy probe 705. Sleeve 750 is secured to vitrectomy probe 705 with an adhesive, such as an optical adhesive. The embodiment of FIG. 7 is also designed to fit through a 23 gauge cannula. However, sleeve 750 takes up some of the cross section area requiring the optical fibers in optical fiber array 710, 715, 720, 725, 730, 735, and 740 to have smaller diameters. In this embodiment, Optical fiber 710 has a diameter of 0.0041 inches, optical fibers 715 and 720 have diameters of 0.0039 inches, optical fibers 725 and 730 have diameters of 0.0035 inches, and optical fibers 735 and 740 have diameters of 0.0029 inches. The resulting cross section area (about 42,400 microns) provides a luminous flux of about 11.5 (using an AHBI illuminator with 100% efficiency at coupling). As in FIG. 5, all of this light is concentrated around the cutting port of the vitrectomy probe.

Figure 8:
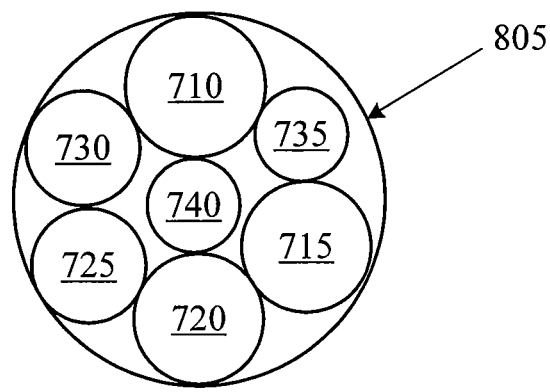
FIG. 8 is a cross section view of an optical fiber array used with an illuminated vitrectomy probe according to an embodiment of the present invention.

FIG. 8 is cross section view of an optical fiber array used with an illuminated vitrectomy probe according to an embodiment of the present invention. The embodiment of FIG. 6 depicts the proximal end of optical fiber array 710, 715, 720, 725, 730, 735, and 740. This end of optical fiber array 710, 715, 720, 725, 730, 735, and 740 is coupled to the 0.63 NA optical fiber 420 as depicted in FIG. 4. Optional cladding or sheathing 805 is also depicted.

Figure 9A:
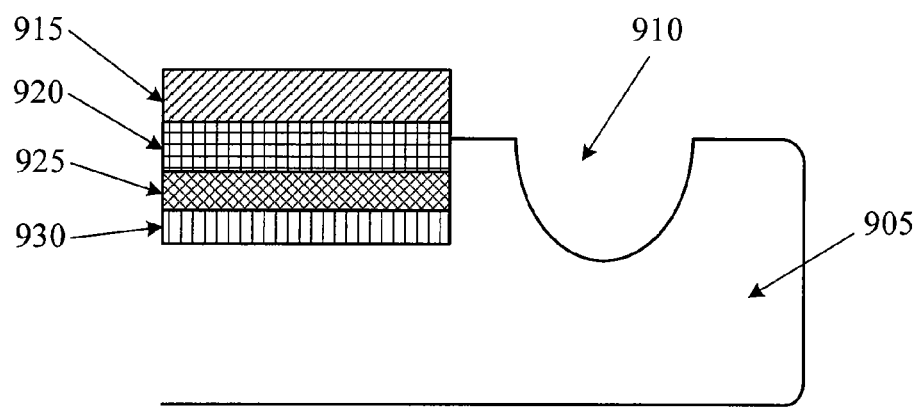
FIG. 9A is side view of an illuminated vitrectomy probe according to an embodiment of the present invention.
Figure 9B:
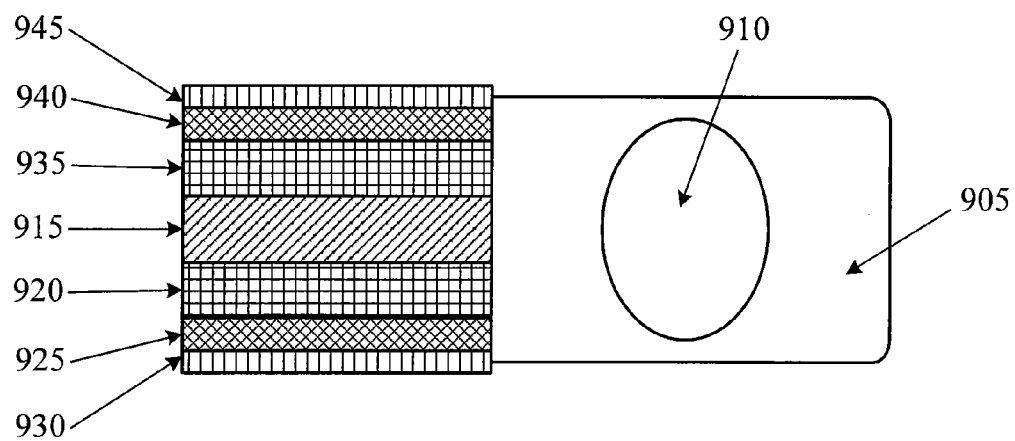
FIG. 9B is top view of an illuminated vitrectomy probe according to an embodiment of the present invention.

FIG. 9A is side view of an illuminated vitrectomy probe according to an embodiment of the present invention, and FIG. 9B is top view of an illuminated vitrectomy probe according to an embodiment of the present invention. FIGS. 9A and 9B provide a different view of the arrangement of the optical fibers shown in FIGS. 5 and 7. Port 910 is located near the end of cannula 905. Port 910 is the cutting port of a vitrectomy probe. Accordingly, concentrating light around port 910 is desirable because it allows the surgeon to see the eye structures near the cutting mechanism of the vitrectomy probe. Conversely, light that is not concentrated around port 910 is wasted.

In the embodiment of FIGS. 9A and 9B, an optical fiber array has seven optical fibers 915, 920, 925, 930, 935, 940, and 945. The seven optical fibers 915, 920, 925, 930, 935, 940, and 945 of the optical fiber array are arranged around the top of cannula 905 near port 910. Optical fiber 915 has the largest diameter, and optical fibers 930 and 945 have the smallest diameters. The diameters of optical fibers 925 and 940 are larger than the diameters of optical fibers 930 and 945 and smaller than the diameters of optical fibers 920 and 935. The diameters of optical fibers 920 and 935 are larger than the diameters of optical fibers 925 and 940 and smaller than the diameter of optical fiber 915. This arrangement has been found to provide a sufficient amount of light near the cutting port 910 of a vitrectomy probe, while maintaining a small (23 gauge) profile.

While the examples provided herein describe an illuminated vitrectomy probe that fits through a 23 gauge cannula, it will be appreciated that the same arrangement of a vitrectomy probe and optical fiber array can be applied to cannulas of other sizes. For example, an optical fiber array of seven fibers can be arranged around a vitrectomy probe in the same way described herein to fit through a 20 gauge cannula, or even through cannulas smaller than 23 gauge. For example, as the diameter of a vitrectomy probe decreases, more cross section area is available for illumination. An illuminated vitrectomy probe that fits through a 25 gauge cannula can have the same optical fiber array configuration described herein.

More generally, the same principles described with respect to the illuminated vitrectomy probe of the preceding figures can be applied to any surgical instrument designed to fit through a small gauge cannula. For example, in ophthalmic surgery, scissors, forceps, aspiration probes, retinal picks, delamination spatulas, various cannulas, and the like may also benefit from targeted illumination. These instruments are designed to fit through small gauge cannulas that are inserted through the sclera during ophthalmic surgery. For each of these instruments, targeted illumination around the working end of the instrument is beneficial.

Figure 10A:
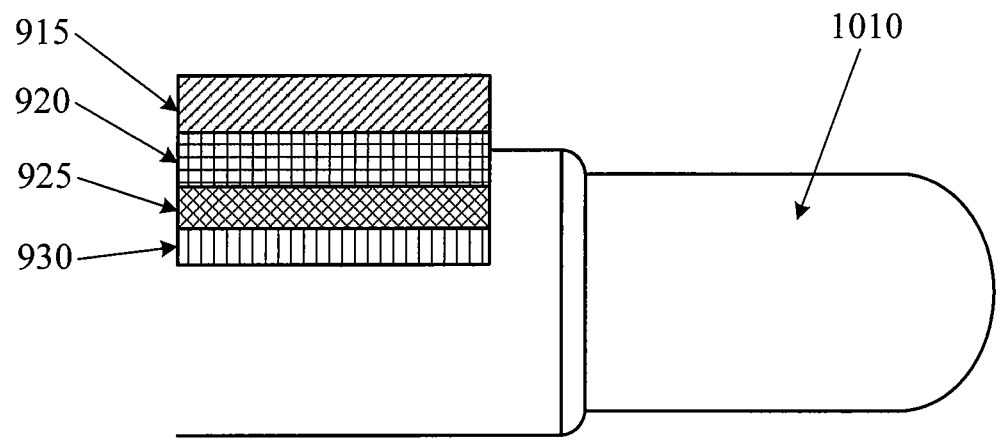
FIG. 10A is side view of a pair of illuminated endo-ophthalmic forceps according to an embodiment of the present invention.
Figure 10B:
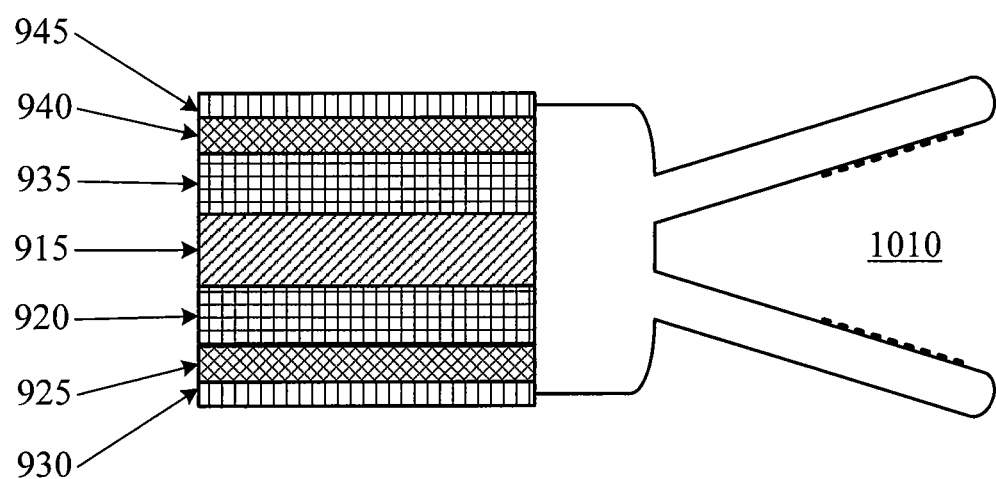
FIG. 10B is top view of a pair of illuminated endo-ophthalmic forceps according to an embodiment of the present invention.

For example, FIG. 10A is side view of illuminated endo-ophthalmic forceps according to an embodiment of the present invention, and FIG. 10B is a top view of illuminated endo-ophthalmic forceps according to an embodiment of the present invention. FIGS. 10A and 10B provide a view of the arrangement of the optical fibers for forceps that is similar to that described with respect to the illuminated vitrectomy probe of FIGS. 5-9. Forceps 1010 include a pair of jaws that are designed to move together to hold eye tissues. Accordingly, targeting light around forceps 1010 is desirable because it allows the surgeon to see the eye structures near the holding mechanism of the forceps. In the embodiment of FIGS. 10A and 10B, light is concentrated on one side of the forceps 1010 as shown, so that a surgeon can more easily see the structure that is located between the jaws of the forceps. Alternatively, the optical fibers 915, 920, 925, 930, 935, 940, and 945 can be positioned to provide backlighting, for example, to provide illumination on the retina.

In the embodiment of FIGS. 10A and 10B, an optical fiber array has seven optical fibers 915, 920, 925, 930, 935, 940, and 945. The seven optical fibers 915, 920, 925, 930, 935, 940, and 945 of the optical fiber array are arranged around the top of forceps 1010. Optical fiber 915 has the largest diameter, and optical fibers 930 and 945 have the smallest diameters. The diameters of optical fibers 925 and 940 are larger than the diameters of optical fibers 930 and 945 and smaller than the diameters of optical fibers 920 and 935. The diameters of optical fibers 920 and 935 are larger than the diameters of optical fibers 925 and 940 and smaller than the diameter of optical fiber 915. This arrangement has been found to provide a sufficient amount of light near the working end of the forceps 1010, while maintaining a small (23 gauge) profile. In this case, forceps 1010, like vitrectomy probe cannula 905, has a circular cross section.

The same arrangement of optical fibers can be applied to any surgical instrument with a generally circular cross section. In this manner, illumination can be targeted to a certain area (typically the working end of the instrument considering the orientation of the instrument in the eye) to provide light where it is needed. For example, in ophthalmic surgery, scissors, forceps, aspiration probes, retinal picks, delamination spatulas, various cannulas, and the like may benefit from targeted illumination. Providing light to the working area of the instrument or to the eye structure with which the instrument interfaces allows the surgeon to better see during surgery.

Figure 11:
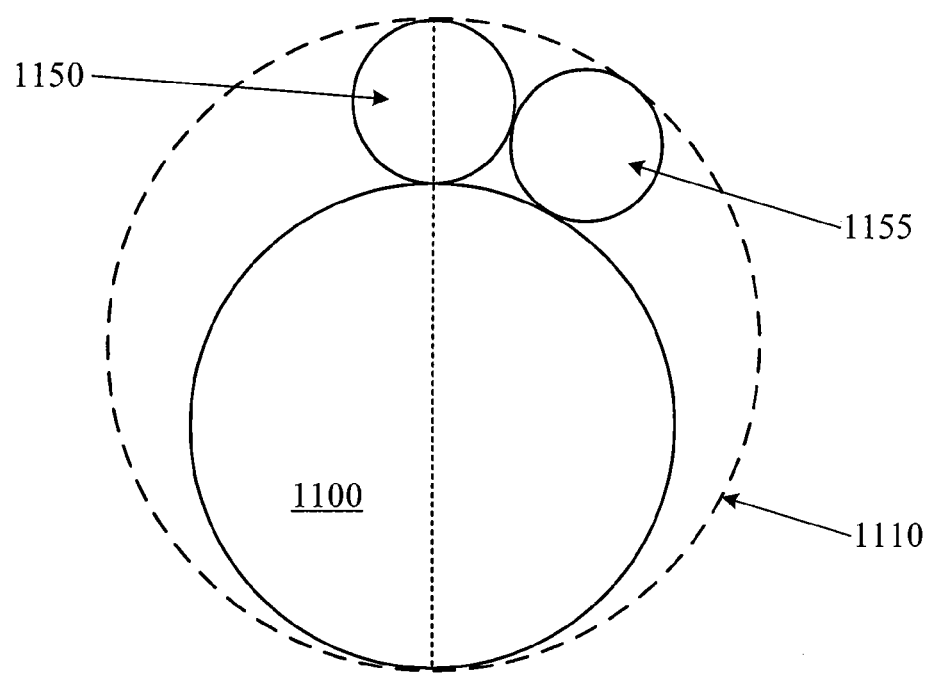
FIG. 11 is a cross section view of an optical fiber array used with a surgical instrument with a generally circular cross section according to an embodiment of the present invention.

FIG. 11 is a cross section view of an optical fiber array used with a surgical instrument with a generally circular cross section according to an embodiment of the present invention. In FIG. 11, generally circular instrument 1100 (represented by a circle) must fit through a small gauge cannula 1110 (also represented by a circle) in order to enter the eye. The radius of the cannula, $r_1$, is larger than the radius of the instrument, $r_2$. The available area for illumination is easily calculated: $\pi(r_1^2-r_2^2)$. In this case, this area is best used for illumination by locating instrument 1100 on an interior surface of cannula 1110 as shown. The largest optical fiber that can then fit in the resulting volume is optical fiber 1150. The center point of optical fiber 1150 and the center point of instrument 1100 lie along the same line in FIG. 11 (dotted line). The circle representing optical fiber 1150 is tangential to the circle representing instrument 1100 and the circle representing cannula 1110. Specific measurements depend on the diameter of instrument 1100 and cannula 1110.

With the first optical fiber 1150 in place, subsequent optical fibers, such as optical fiber 1155, can be positioned. In this example, the largest possible diameter optical fibers are used to fill the available space between the outside of instrument 1100 and the inside of cannula 1110. Generally larger diameter optical fibers have greater capacity for transporting luminous flux through the fiber. With optical fiber 1150 in place, optical fiber 1155 is positioned such that the circle representing it is tangential to the circle representing optical fiber 1150, the circle representing instrument 1100, and the circle representing cannula 1110. This is most easily done using a CAD-type drawing program to approximate the diameter of optical fiber 1155. The size and position of other optical fibers can be determined in a like manner.

Figure 12:
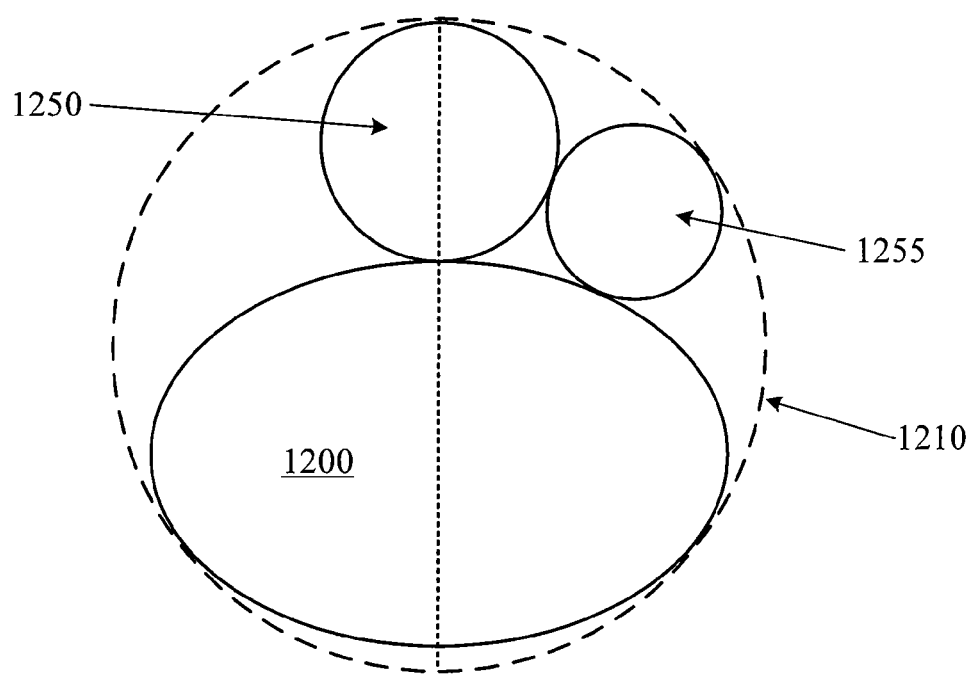
FIG. 12 is a cross section view of an optical fiber array used with a surgical instrument with a generally elliptical cross section according to an embodiment of the present invention.

FIG. 12 is a cross section view of an optical fiber array used with a surgical instrument with a generally elliptical cross section according to an embodiment of the present invention. The same principles described with respect to the generally circular instrument of FIG. 11 also apply to the generally elliptical instrument of FIG. 12. Instrument 1200, represented by an ellipse, is located in small gauge cannula 1210 so that the area between instrument 1200 and cannula 1210 is maximized on one side and minimized on the other. In this position, instrument 1200 contacts the interior surface of cannula 1210 along two lines contained along the cylinder of cannula 1210. With the location of instrument 1200 fixed, the circle representing optical fiber 1250 is located such that it is tangential to the ellipse representing instrument 1200 and the circle representing cannula 1210. The diameter of the circle representing optical fiber 1250 and the minor diameter of the ellipse representing instrument 1200 lie along the same line (dotted line).

Figure 13:
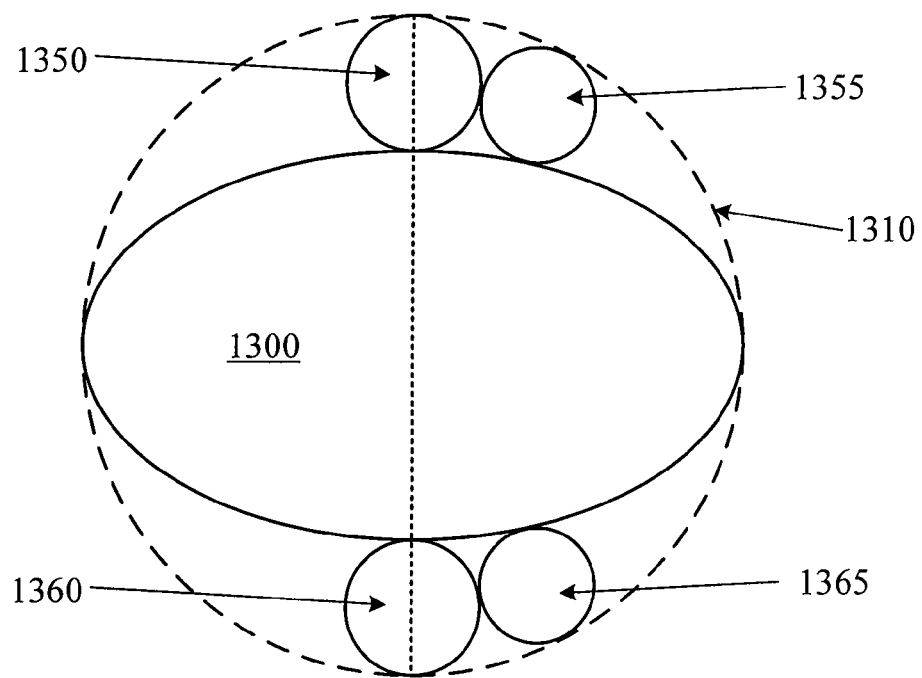
FIG. 13 is a cross section view of an optical fiber array used with a surgical instrument with a generally elliptical cross section according to an embodiment of the present invention.

FIG. 13 is a cross section view of an optical fiber array used with a surgical instrument with a generally elliptical cross section according to an embodiment of the present invention. In the embodiment of FIG. 13, targeted illumination is provided in two locations. Optical fibers 1350 and 1355 (and others not shown) provide illumination on top of instrument 1300, while optical fibers 1360 and 1365 (and others not shown) provide illumination on top of instrument 1300. Cannula 1310 is also depicted. The optical fibers are selected and positioned using the same principles described above.

Figure 14:
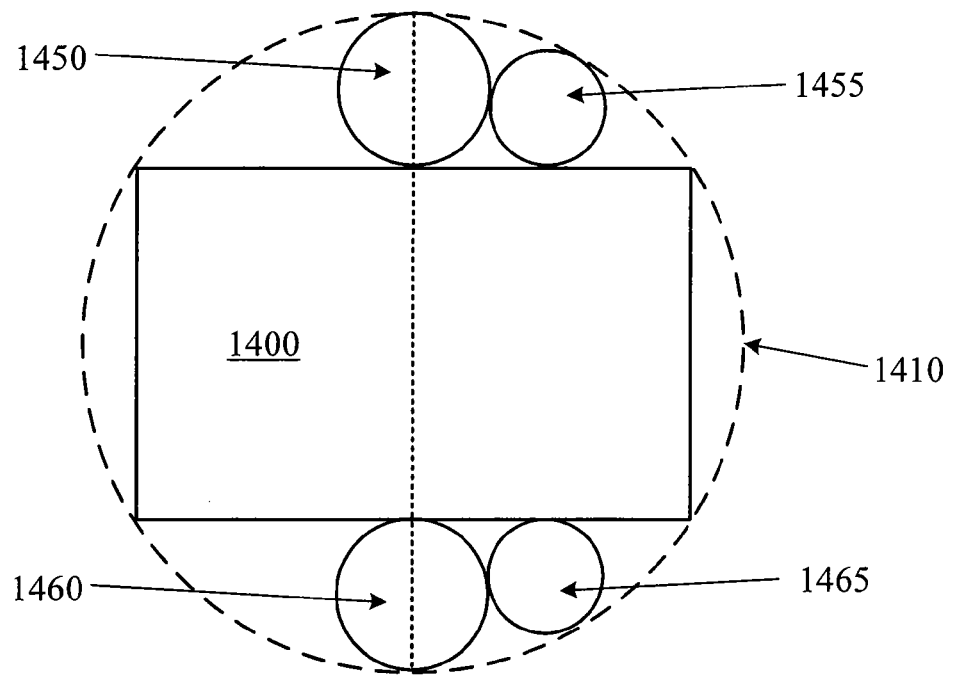
FIG. 14 is a cross section view of an optical fiber array used with a surgical instrument with a generally rectangular cross section according to an embodiment of the present invention.

FIG. 14 is a cross section view of an optical fiber array used with a surgical instrument with a generally rectangular cross section according to an embodiment of the present invention. Again, two areas are targeted for illumination. Optical fibers 1450 and 1455 (and others not shown) provide illumination on top of instrument 1400, while optical fibers 1460 and 1465 (and others not shown) provide illumination on top of instrument 1400. Cannula 1410 is also depicted. The optical fibers are selected and positioned using the same principles described above.

The same principles can be applied to an instrument of any cross section. In addition, instruments may be approximated by geometrical shapes. For example, an instrument that has an oblong cross section can be approximated by an ellipse. Of course, the location of the targeted illumination corresponds to the location of the optical fibers. While the fibers are generally selected to maximize light throughput, their location can be adjusted for a given instrument. Further, while the optical fibers are depicted as having a generally circular cross section, optical fibers and light guides with other cross sections may also be employed.

From the above, it may be appreciated that the present invention provides an improved illuminated vitrectomy probe. Arranging an array of optical fibers near the working area of a surgical instrument provides light that is usable by the surgeon during surgery. In addition, the present invention most effectively utilizes the small cross sectional area available to carry an optical fiber array. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. An illuminated vitrectomy probe comprising:
   a vitrectomy probe having a cutting port disposed at a distal end of a cannula; and
   an array of optical fibers terminating near the cutting port, the array of optical fiber comprising:
      a first optical fiber; and
      a plurality of optical fibers flanking the first optical fiber on opposite sides thereof, the first optical fiber having a diameter larger than the diameters of the flanking optical fibers, the array of optical fibers arranged along the cannula such that the flanking optical fibers have progressively decreasing diametrical sizes away from the first optical fiber,
   the array of optical fibers located adjacent to the cannula only on a side of the cannula on which the cutting port is located.

2. The illuminated vitrectomy probe of claim 1 wherein the array of optical fibers and cannula are configured to fit through a second cannula with a size not greater than 23 gauge.

3. The illuminated vitrectomy probe of claim 2 in which the array of optical fibers comprises seven optical fibers with diameters between 0.003 inches and 0.005 inches.

4. The illuminated vitrectomy probe of claim 1 wherein the array of optical fibers comprises optical fibers with diameters between 0.003 inches and 0.005inches.

5. The illuminated vitrectomy probe of claim 1 further comprising:
 a potting substance that holds the optical fibers against the cannula of the vitrectomy probe.

6. The illuminated vitrectomy probe of claim 1 further comprising:
 a sleeve that holds the optical fibers against the cannula of the vitrectomy probe.

7. The illuminated vitrectomy probe of claim 6 wherein the array of optical fibers comprises optical fibers with diameters between 0.002 inches and 0.005 inches.

8. The illuminated vitrectomy probe of claim 1 further comprising:
 a housing having an opening through which the array of optical fibers passes, the housing attached to the cannula.

9. The illuminated vitrectomy probe of claim 1 wherein the array of optical fibers are disposed in a semi-circular pattern around the cannula near the cutting port.

10. The illuminated vitrectomy probe of claim 1 further comprising:
 a coupling for coupling an end of the array of optical fibers to a light source.

* * * * *